United States Patent
Hills et al.

(10) Patent No.: US 8,391,440 B2
(45) Date of Patent: Mar. 5, 2013

(54) CURTAIN ASSEMBLY, SCANNING SYSTEM, AND METHOD FOR ASSEMBLING SCANNING SYSTEM

(75) Inventors: Steven Leslie Hills, San Jose, CA (US); Nicholas Bantle Masson, Berkeley, CA (US)

(73) Assignee: Morpho Detection, Inc., Newark, CA (US)

( * ) Notice: Subject to any disclaimer, the term of this patent is extended or adjusted under 35 U.S.C. 154(b) by 582 days.

(21) Appl. No.: 12/635,926

(22) Filed: Dec. 11, 2009

(65) Prior Publication Data

US 2011/0142195 A1 Jun. 16, 2011

(51) Int. Cl.
*G01N 23/04* (2006.01)
(52) U.S. Cl. .......................................... 378/57; 378/203
(58) Field of Classification Search .............. 378/57, 378/203
See application file for complete search history.

(56) References Cited

U.S. PATENT DOCUMENTS

| | | | |
|---|---|---|---|
| 4,239,969 A | 12/1980 | Haas et al. | |
| 6,872,001 B1 | 3/2005 | Gilevich | |
| 7,151,817 B1 * | 12/2006 | Abraham et al. | 378/57 |
| 2002/0071522 A1 * | 6/2002 | Fenkart et al. | 378/147 |
| 2005/0185757 A1 * | 8/2005 | Kresse et al. | 378/57 |
| 2009/0041187 A1 | 2/2009 | Peschmann et al. | |

* cited by examiner

*Primary Examiner* — Glen Kao
(74) *Attorney, Agent, or Firm* — Armstrong Teasdale LLP

(57) ABSTRACT

A curtain assembly includes at least one curtain including at least one slat. The at least one curtain is configured to be rotatably coupled to a housing of a scanning system having a radiation source and a detector. The at least one curtain is further configured to facilitate drawing an object into the scanning system housing while substantially preventing radiation emitted from the radiation source from exiting the housing through the at least one curtain.

20 Claims, 7 Drawing Sheets

FIGURE 8              FIGURE 9

CURTAIN ASSEMBLY, SCANNING SYSTEM, AND METHOD FOR ASSEMBLING SCANNING SYSTEM

BACKGROUND OF THE INVENTION

1. Field of the Invention

The subject matter described herein relates generally to scanning systems, such as computed tomography (CT) scanning systems, and, more particularly, to CT scanning systems that shield an external environment from radiation.

2. Description of Related Art

At least some known explosive detection systems use tomographic systems to scan a continuous stream of objects. In at least one known explosive detection system, a machine control for a scanning device generally receives information, such as an identification tag, about each object from an external system that transports the objects into a scanning device, such as a CT scanning system. At least one CT scanning system includes passive curtains to shield an external environment from X-ray radiation produced by the CT scanning system. However, objects passing through the passive curtains may be repositioned, such as by moving adjacent each other or shifting orientation, before and/or inside the scanning device. Such repositioning may cause confusion between the extent of an object as externally measured, and the extent and position of the object once inside the scanning device. As such, there is a need to provide curtains that shield an external environment from radiation and that facilitate reducing a repositioning of objects passing through the scanning device.

BRIEF SUMMARY OF THE INVENTION

In one aspect, a curtain assembly is provided that includes at least one curtain including at least one slat. The at least one curtain is configured to be rotatably coupled to a housing of a scanning system having a radiation source and a detector. The at least one curtain is further configured to facilitate drawing an object into the scanning system housing while substantially preventing radiation emitted from the radiation source from exiting the housing through the at least one curtain.

In another aspect, a scanning system is provided. The scanning system includes a housing that defines an examination space and at least one curtain. The at least one curtain includes at least one slat and the at least one curtain is rotatably coupled to the housing. The scanning system also includes a conveyor configured to transport a stream of objects through the examination space, a radiation source configured to emit radiation through the examination space, and a detector configured to detect radiation emitted from the radiation source.

In yet another aspect, a method of assembling a scanning system is provided. The scanning system including a housing and a radiation source configured to emit radiation within the scanning system. The method includes coupling at least one slat to at least one top portion to form at least one curtain and rotatably coupling the at least one curtain to the housing. The at least one curtain is configured to facilitate drawing an object into the housing and to substantially prevent radiation from the radiation source from exiting the scanning system through the at least one curtain.

The embodiments described herein use a curtain assembly to shield an external environment from radiation emitted within a scanning system. Moreover, the curtain assembly facilitates drawing objects into the scanning system, and facilitates reducing a repositioning of objects as objects advance through the scanning system. In one embodiment, the curtain assembly includes two groups of curtains that facilitate preventing radiation from escaping the scanning system while objects are being drawn through the scanning system.

BRIEF DESCRIPTION OF THE DRAWINGS

FIGS. 1-9 show exemplary embodiments of the systems and method described herein.

DETAILED DESCRIPTION OF THE INVENTION

The embodiments described herein use a curtain assembly to shield an external environment from radiation emitted within a computed tomography (CT) scanning system. Moreover, the curtain assembly facilitates drawing objects into the CT scanning system, and facilitates reducing a repositioning of objects as objects advance through the CT scanning system. In one embodiment, the rotatable curtain assembly includes two groups of curtains that facilitate preventing radiation from escaping the CT scanning system while objects are being drawn through the CT scanning system.

An embodiment of an inspection system constructed in accordance with the principles of the invention provides radiation shielding on the entrance and/or exit of detection machines that use radiation sources to inspect objects, such as packages or bags. A series of curtain assemblies rotate as the objects are loaded into and/or out of the detection machine. The rotation of the curtain assemblies helps draw the objects into and/or out of the detection machine. Each curtain assembly comprises a top portion from which radiation damping slats hang down to form a continuous, or near continuous, enclosure having a cavity therein. There are at least two embodiments, an active one where the curtain assemblies are driven by a motor; and a passive one where the curtain assemblies are free to rotate under the force of the objects entering and/or exiting the detection machine on a conveyor. These and/or additional embodiments are described in more detail below.

Although described in detail in a CT inspection setting, it is contemplated that the benefits accrue to all imaging modalities including, for example, Electron Beam CT (EBCT), Positron Emission Tomography (PET), Single Photon Emission Computed Tomography (SPECT), X-ray Tomo-synthesis, and in both non-medical settings and medical settings. Examples of non-medical settings include, but are not limited to: security checkpoints, baggage scanning systems, and container inspection systems.

Figure 1:
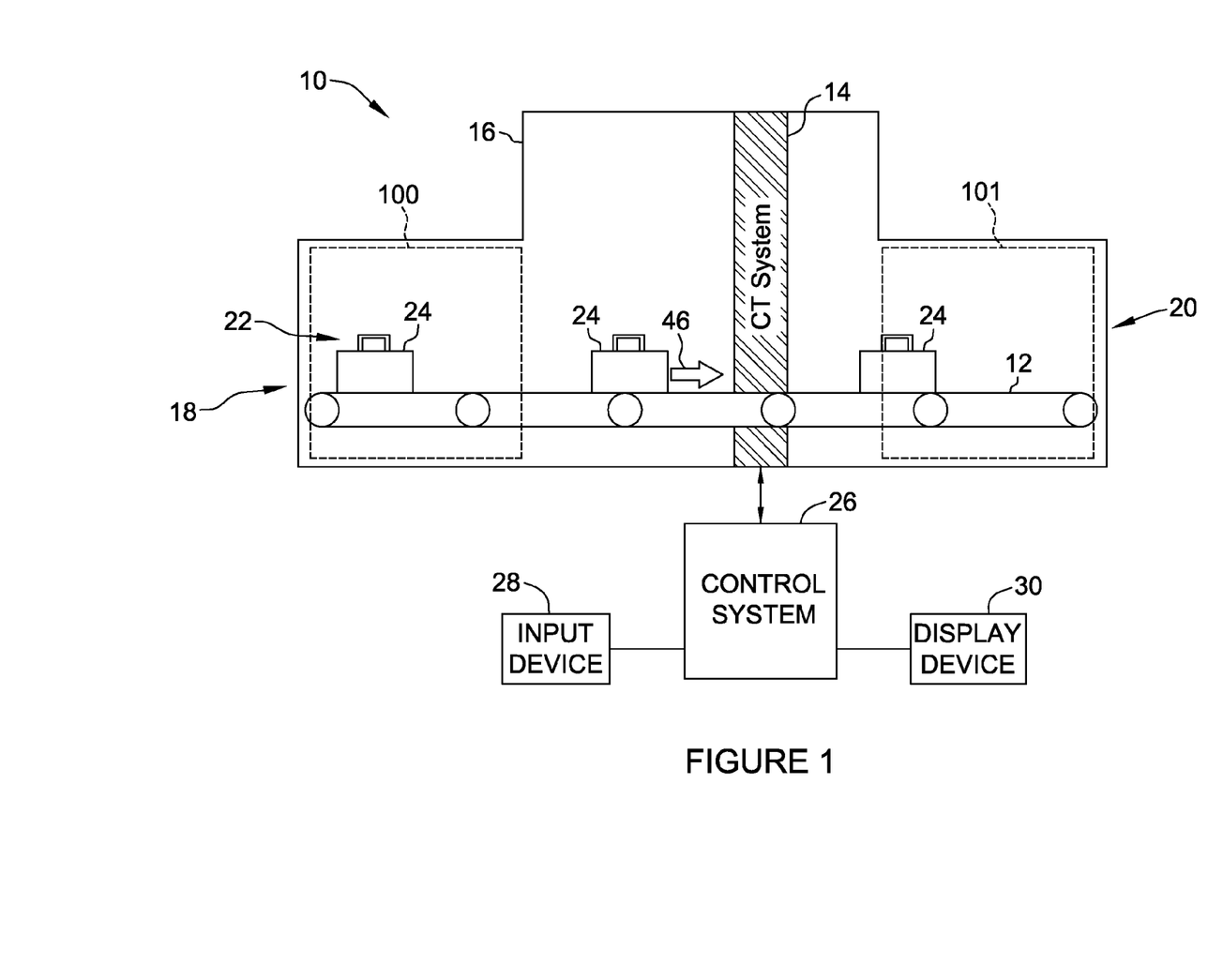
FIG. 1 is a schematic view of an exemplary scanning system.

FIG. 1 is a schematic view of an exemplary scanning system 10. Scanning system 10 includes a conveyor 12 and a CT system 14 positioned at least partially within a housing 16. Conveyor 12 extends between an inlet 18 of housing 16 and an outlet 20 of housing 16. Further, conveyor 12 is configured to transport a stream 22 of objects 24 through scanning system 10. In the exemplary embodiment, stream 22 includes at least one object 24. Conveyor 12 extends through CT system 14 and conveys objects 24 sequentially through CT system 14 such that each object 24 is scanned by CT system 14. CT system 14 is configured to scan objects 24 one at a time in the exemplary embodiment.

A control system 26 is in operational control communication with conveyor 12 and CT system 14. As used herein, "operational control communication" refers to a link, such as a conductor, a wire, and/or a data link, between two or more components of scanning system 10 that enables signals, electric currents, and/or commands to be communicated between the two or more components. The link is configured to enable one component to control an operation of another component of scanning system 10 using the communicated signals, electric currents, and/or commands. Further, as used herein, the term "control system" is not limited to integrated circuits referred to in the art as a control system, but broadly refers to a computer, a microcontroller, a microcomputer, a programmable logic controller, an application specific integrated circuit, and/or any other programmable circuit configured or programmed to control operation of the system components.

Control system 26 includes a central processing unit and may include a device, such as a floppy disk drive or a compact-disc read-only memory (CD-ROM) drive, for reading data from a computer-readable medium, such as a floppy disk, a compact disc-read only memory (CD-ROM), a magneto-optical disk (MOD), and/or a digital versatile disc (DVD). In an alternative embodiment, control system 26 executes instructions stored in firmware. In the exemplary embodiment, control system 26 controls speed, acceleration, deceleration, starting, stopping, and/or any suitable function of conveyor 12. Moreover, control system 26 controls CT system 14 and/or conveyor 12 to acquire data relating to objects 24, as described in more detail below. In the exemplary embodiment, control system 26 is also in communication with an input device 28 and a display device 30. Display device 30 may include, without limitation, a liquid crystal display (LCD), a cathode ray tube (CRT), and/or any suitable output device. Input device 28 may include, without limitation, a mouse and a keyboard.

As more fully described herein, scanning system 10 includes at least one curtain assembly configured to prevent or limit radiation emission from scanning system 10. In the exemplary embodiment, scanning system 10 includes a first curtain assembly 100 that is positioned within housing 16 and proximate inlet 18. Scanning system 10 also includes a second curtain assembly 101 that is positioned within housing 16 and proximate outlet 20.

Figure 2:
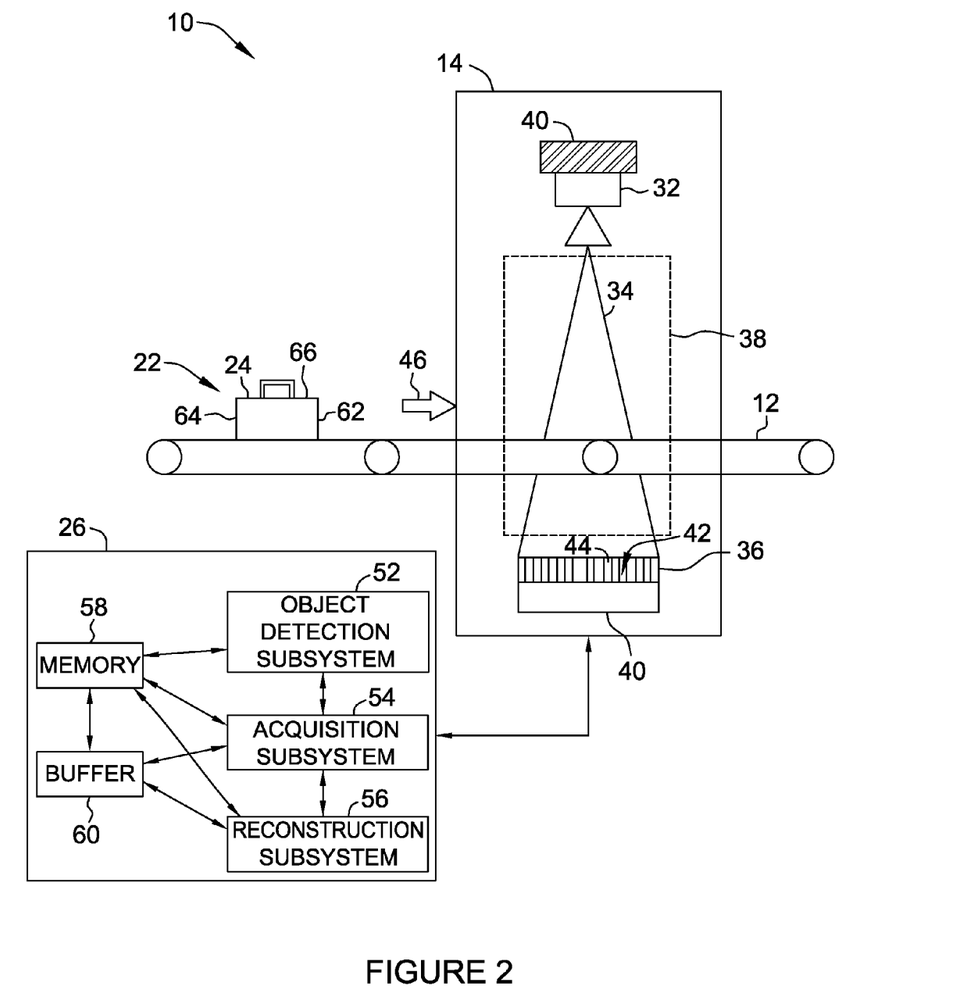
FIG. 2 is a schematic view of an exemplary computed tomography (CT) scanning system that may be used with the scanning system shown in FIG. 1.

FIG. 2 is a schematic view of an exemplary CT system 14 suitable for use with scanning system 10 (shown in FIG. 1). CT system 14 includes a radiation source 32 for emitting radiation 34 and a detector 36 for detecting emitted radiation 34. A CT plane 38 (sometimes referred to as an "examination space") is defined between radiation source 32 and detector 36. As used herein, CT plane 38 is not limited to a strictly planar region, but may, in alternative embodiments, also encompass, for example, a conical region, a fan-shaped region, or any suitably-shaped region. In the exemplary embodiment, radiation source 32 and detector 36 are coupled to a gantry 40 for rotation about CT plane 38. Alternatively, radiation source 32 and/or detector 36 are coupled within CT system 14 such that radiation source 32 and/or detector 36 are stationary with respect to CT plane 38. In the exemplary embodiment, CT system 14 performs a continuous helical scan as stream 22 of objects 24 passes through CT plane 38.

In the exemplary embodiment, control system 26 is in operational control communication with radiation source 32 and detector 36. Control system 26 controls emission of radiation 34 from radiation source 32 and receives data from detector 36. Further, control system 26 controls operation of components of CT system 14. In the exemplary embodiment, radiation source 32 emits radiation 34 as X-rays in a cone-beam. Alternatively, radiation source 32 may emit any suitable radiation having any suitable beam shape, such as a fan beam.

Detector 36 includes a plurality of rows 42 and columns (not shown) of detector elements 44. Each row 42 extends in a direction that is substantially perpendicular to a direction of object travel indicated by directional arrow 46. The columns are substantially parallel to the object travel direction indicated by directional arrow 46. Each detector element 44 produces an electrical signal that represents an intensity of an impinging radiation beam and, hence, the attenuation of the beam as the beam passes through object 24. The electrical signals produced by detector elements 44 are transmitted to control system 26.

In the exemplary embodiment, control system 26 includes an object detection subsystem 52, an acquisition subsystem 54, and a reconstruction subsystem 56. Control system 26 also includes a memory 58 for data storage and a buffer 60 for temporary data storage. Although memory 58 and buffer 60 are shown as separate components, it should be understood that memory 58 and buffer 60 may be the same component within control system 26. Memory 58 and/or buffer 60 may be a random access memory (RAM) and/or a read only memory (ROM).

In the exemplary embodiment, object detection subsystem 52 is configured to determine a leading edge 62 and a trailing edge 64 of a first object 66 in stream 22 using radiation 34 detected by detector 36. Acquisition subsystem 54 is configured to process and/or record raw data of first object 66 based on the determination of leading edge 62 and trailing edge 64. Reconstruction subsystem 56 is configured to reconstruct an image of first object 66 using at least the processed and/or recorded raw data.

Figure 3:
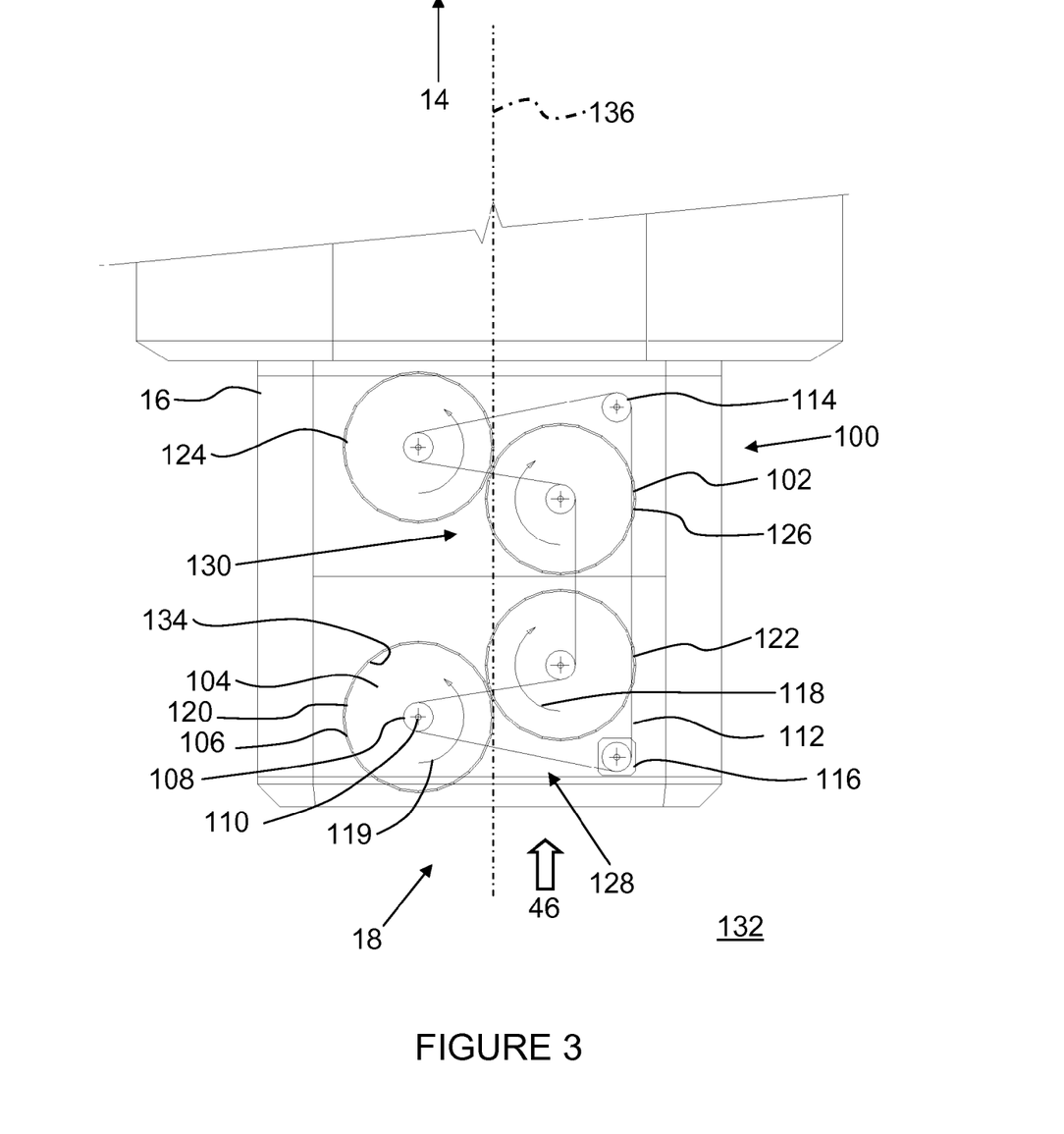
FIG. 3 is a top cut-away view of an exemplary curtain assembly that may be used with the CT scanning system shown in FIG. 2.

FIG. 3 is a cut-away view of an exemplary curtain assembly 100 that may be used with scanning system 10 (shown in FIG. 1) and CT system 14. In the exemplary embodiment, curtain assembly 100 is positioned within housing 16 of scanning system 10. More specifically, curtain assembly 100 is positioned within housing 16 and proximate inlet 18. In an alternative embodiment, at least a portion of curtain assembly 100 is positioned or extends outside of housing 16. In another embodiment, at least a portion of curtain assembly 100 is positioned downstream of inlet 18 with respect to the direction of object travel indicated by directional arrow 46. Second curtain assembly 101 (shown in FIG. 1) is positioned within housing 16 and proximate outlet 20. As described herein, in the exemplary embodiment, second curtain assembly 101 is substantially similar to curtain assembly 100, and the description herein of curtain assembly 100 with respect to inlet 18 applies to second curtain assembly 101 of outlet 20, unless otherwise specified. Alternatively, second curtain assembly 101 may be substantially dissimilar to, or may have a substantially different configuration from, curtain assembly 100.

Curtain assembly 100 includes at least one curtain 102. In the exemplary embodiment, curtain assembly 100 includes four curtains 102. Alternatively, curtain assembly 100 includes any suitable number of curtains 102 that enables scanning system 10 to operate as described herein. Each curtain 102 includes a top portion 104 that is coupled, directly or indirectly, to housing 16. In the exemplary embodiment, top portion 104 is substantially circular or disk-shaped. Alternatively, top portion 104 has any suitable shape that enables curtain 102 to operate as described herein. For example, top portion 104 may have a square shape, a polygonal shape, or an oval shape. In the exemplary embodiment, curtain 102 includes a plurality of slats 106 that are coupled to and hang substantially vertically from an outer perimeter 134 of top portion 104. As used herein, the term "vertically" refers to an orientation substantially parallel to a force of gravity. Alternatively, curtain 102 includes one slat 106 that substantially circumscribes top portion 104. Each slat 106 includes a suitable radiation damping material, such as lead, to facilitate protecting an external environment 132 from radiation 34 emitted within CT system 14.

In the exemplary embodiment, top portion 104 of each curtain 102 is rotatably coupled to housing 16 via a coupling member 108. In the exemplary embodiment, coupling member 108 includes a gear that is rotatably coupled to housing 16. Alternatively, coupling member 108 includes a sprocket, a wheel, a spool, a cylinder, or any suitable device that enables curtain 102 to operate as described herein. In the exemplary embodiment, a rotation of coupling member 108 induces a rotation of curtain 102 with respect to housing 16. In the exemplary embodiment, coupling member 108 is positioned substantially at a center 110 of top portion 104, and is aligned with a centerline (not shown in FIG. 3) of curtain 102.

In the exemplary embodiment, curtain assembly 100 includes a drive chain 112 that is coupled to coupling member 108 of each curtain 102. Drive chain 112 is configured to rotate each curtain 102 via coupling members 108. Alternatively, drive chain 112 is coupled to and configured to rotate only one or more curtains 102 via coupling members 108. In the exemplary embodiment, drive chain 112 includes a chain of metal or other suitable material. Alternatively, drive chain 112 includes a belt, wire, band, rope, or any suitable device that engages coupling member 108 and enables curtain 102 to rotate as described herein. In another embodiment, curtain assembly 100 includes a plurality of drive chains 112, and each drive chain 112 may be coupled to the same curtains 102 as each other drive chain 112, or to different curtains 102 from each other drive chain 112.

Alternatively, as described above, the curtain assembly 100 does not include a drive chain 112 or motor 116. In such embodiment, each curtain 102 is configured to rotate about the curtain centerline when a force is applied to one or more slats 106 and/or to top portion 104 by an object 24 moved by conveyor 12 (both shown in FIG. 1). For example, conveyor 12 may transport an object 24 through inlet 18 and/or through outlet 20 and may cause object 24 to impact one or more slats 106 of curtain 102. Upon such impact, curtain 102 rotates and thereby facilitates enabling object 24 to enter and/or exit CT system 14, because the rotation of curtain 102 is believed to provide less resistance to object 24 than prior types of publically-available non-rotatable shielding curtains.

In the exemplary embodiment, curtain assembly 100 includes at least one tensioning device 114 and at least one motor 116. In the exemplary embodiment, tensioning device 114 is coupled to housing 16 and to drive chain 112. Tensioning device 114 facilitates maintaining a tension in drive chain 112. In the exemplary embodiment, tensioning device 114 includes a gear that is rotatably coupled to housing 16. Alternatively, tensioning device 114 includes a sprocket, a wheel, a spool, a cylinder, or any suitable device that enables curtain assembly 100 to operate as described herein. In the exemplary embodiment, motor 116 is operationally coupled to tensioning device 114 and to coupling members 108 via drive chain 112. Motor 116 propels drive chain 112 counter-clockwise through curtain assembly 100, and drive chain 112 rotates curtains 102 by engaging and rotating coupling members 108. As shown in FIG. 3, motor 116 may induce curtains 102 to rotate in a clockwise direction 118 and/or a counter-clockwise direction 119. In the exemplary embodiment, a first curtain 120 rotates in counter-clockwise direction 119, a second curtain 122 rotates in clockwise direction 118, a third curtain 124 rotates in counter-clockwise direction 119, and a fourth curtain 126 rotates in clockwise direction 118. As such, curtains 102 rotate in complementary directions to facilitate drawing objects 24 through curtain assembly 100. Alternatively, curtains 102, drive chain 112, tensioning device 114, and motor 116 may be configured such that each curtain 102 may rotate in any desired direction.

In another embodiment, one or more motors 116 are positioned within housing 16 and are not coupled to drive chain 112. In such embodiment, motors 116 may be coupled directly to curtains 102 and/or to coupling members 108, or may be coupled to curtains 102 and/or to coupling members 108 indirectly, such as via one or more gears, chains, belts, or any suitable device (not shown).

In the exemplary embodiment, motor 116 is controlled by control system 26 (shown in FIG. 1). In the exemplary embodiment, control system 26 operates motor 116 while conveyor 12 is moving, and deactivates motor 116 when conveyor 12 stops. Alternatively, control system 26 may operate conveyor 12 and motor 116 independently of each other.

In the exemplary embodiment, curtain assembly 100 includes a front group 128 of curtains 102 and a rear group 130 of curtains 102 that facilitate protecting external environment 132 from radiation 34 emitted within CT system 14. More specifically, object 24 may displace one or more slats 106 of one or more curtains 102 within front group 128 of curtains 102, but rear group 130 of curtains 102 may remain substantially undisturbed until object 24 has substantially moved past front group 128. Similarly, when object 24 has substantially moved past front group 128 and begins to impact one or more curtains 102 of rear group 130, one or more slats 106 of curtains 102 within front group 128 may return to their original position to facilitate blocking radiation 34 from escaping housing 16. As such, an ability to protect external environment 132 from CT system 14 radiation may remain substantially intact, even when objects are being moved through the curtain assemblies. In the exemplary embodiment, front group 128 includes first curtain 120 and second curtain 122, and rear group 130 includes third curtain 124 and fourth curtain 126. Alternatively, front group 128 and/or rear group 130 may include any suitable number and/or arrangement of curtains 102.

In the exemplary embodiment, curtain assembly 100 is positioned about a centerline 136 of housing 16. More specifically, first curtain 120 and second curtain 122 are positioned opposite each other about centerline 136, and third curtain 124 and fourth curtain 126 are positioned opposite each other about centerline 136. As shown in FIG. 3, a portion of first curtain 120, second curtain 122, third curtain 124, and/or fourth curtain 126 may overlap centerline 136. Alternatively, one or more curtains 102 of curtain assembly 100 are positioned off-center with respect to centerline 136.

Figure 4:
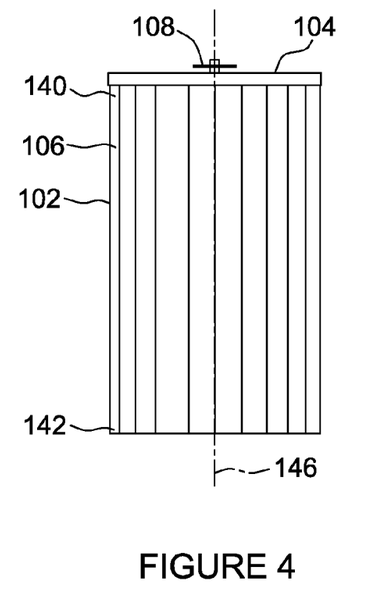
FIG. 4 is a side view of an exemplary curtain that may be used with the curtain assembly shown in FIG. 3.
Figure 5:
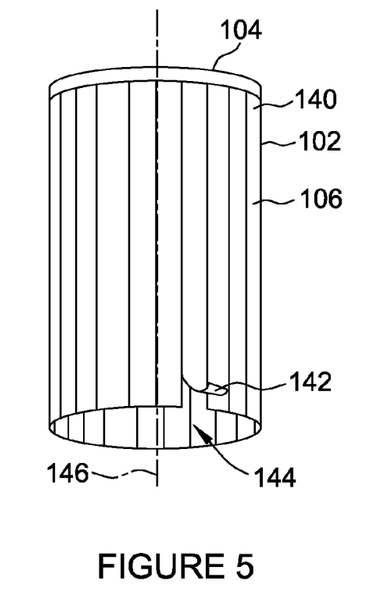
FIG. 5 is a perspective view of the curtain shown in FIG. 4.

FIGS. 4 and 5 show a side view and a perspective side view, respectively, of an exemplary curtain 102 that may be used with curtain assembly 100 (shown in FIG. 3). Each slat 106 of curtain 102 includes a slat top 140 and a slat bottom 142. In the exemplary embodiment, slat tops 140 are coupled to, and substantially circumscribe, top portion 104, and slat bottoms 142 hang freely. Alternatively, one or more slat bottoms 142 are coupled together by a ring or other coupling device (not shown). In the exemplary embodiment, each slat 106 abuts, or partially overlaps, each adjacent slat 106 such that slats 106 at least partially define a cavity 144 within curtain 102. In the exemplary embodiment, slats 106 are positioned substantially equidistant from a centerline 146 that extends longitudinally through curtain 102 and cavity 144. In the exemplary embodiment, cavity 144 is formed with a substantially cylindrical shape. Alternatively, cavity 144 is formed with any suitable shape that enables curtain assembly 100 to operate as described herein.

Figure 6:
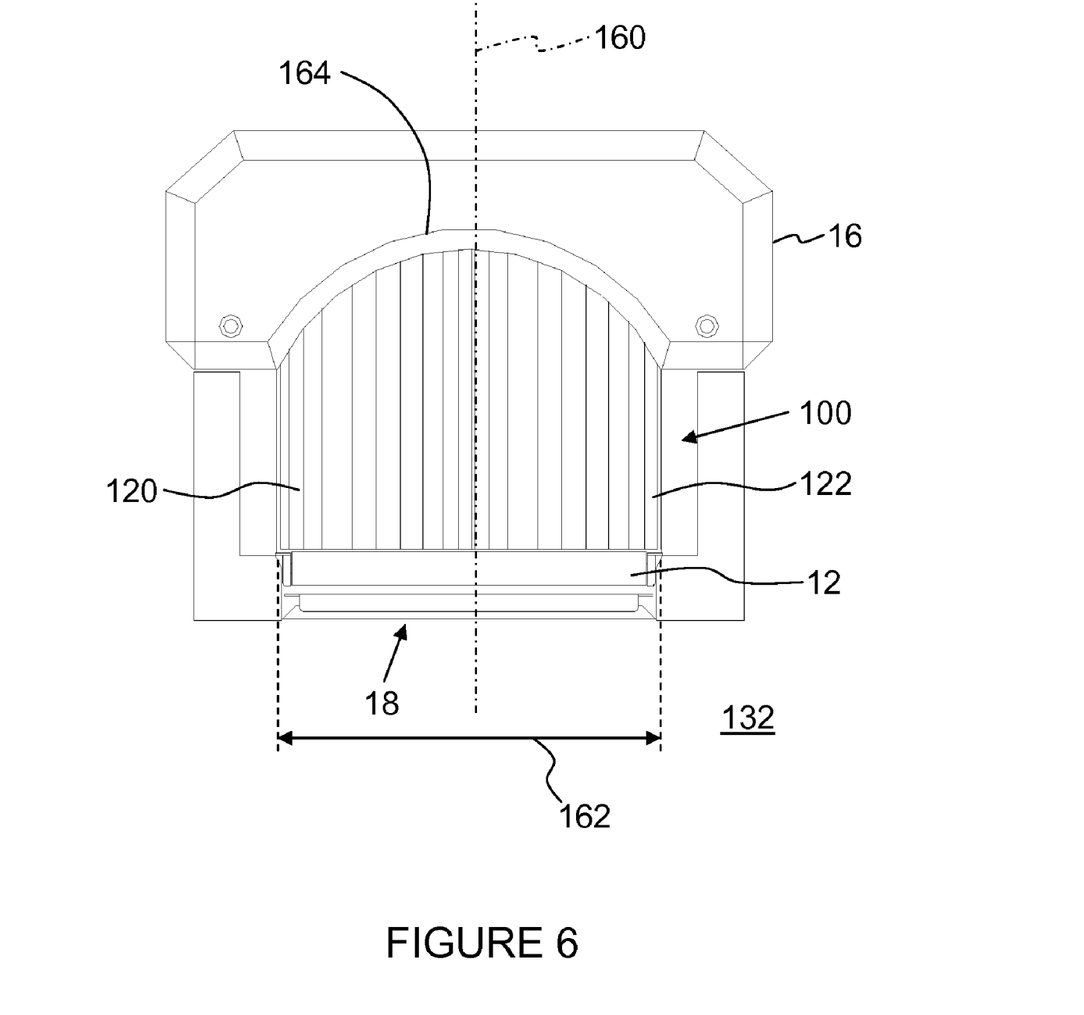
FIG. 6 is a front view of the curtain assembly shown in FIG. 3.

FIG. 6 illustrates a front view of curtain assembly 100 and housing 16. In the exemplary embodiment, curtain assembly 100 is positioned about a centerline 160 at or near inlet 18. Alternatively, one or more curtains 102 of curtain assembly 100 are positioned off-center with respect to centerline 160. In the exemplary embodiment, curtains 102 extend along a width 162 of inlet 18 such that curtains 102 substantially fill width 162. Moreover, curtains 102 extend from a top 164 of inlet 18 to conveyor 12 such that curtains 102 substantially block inlet 18. As such, curtains 102 facilitate blocking and/or absorbing radiation 34 from radiation source 32 to reduce or prevent radiation 34 from exiting housing 16 through inlet 18.

During operation, conveyor 12 transports a stream 22 of objects 24 to CT system 14 and, more specifically, to inlet 18 of housing 16. As each object enters inlet 18, object 24 impacts one or more slats 106 of first curtain 120 and/or one or more slats 106 of second curtain 122. Slats 106 are flexible, such that at least a portion of slats 106, such as slat bottoms 142, may flex and/or move horizontally and/or vertically as object 24 impacts slats 106. Moreover, because slats 106 are flexible, object 24 may move past or through one or more cavities 144 of curtains 102. As conveyor 12 transports objects 24 to CT system 14, motor 116 propels drive chain 112 through curtain assembly 100. Drive chain 112 rotates curtains 102 via coupling members 108. Due to the complementary rotations of first and second curtains 120 and 122, slats 106 wrap around object 24 and draw object 24 further into curtain assembly 100. Object 24 impacts third curtain 124 and/or fourth curtain 126. Due to the complementary rotations of third and fourth curtains 124 and 126, object 24 is drawn through curtain assembly 100 into CT plane 38 (shown in FIG. 2).

As object 24 enters CT plane 38, object 24 is scanned by CT system 14. More specifically, radiation source 32 emits radiation 34 through CT plane 38, and detector 36 measures an amount of radiation 34 received from radiation source 32, after radiation 34 is attenuated by object 24. As a consequence of scanning object 24, a portion of radiation 34 may scatter in different directions, such as towards inlet 18 and/or towards outlet 20. Due to the configuration of curtains 102, and the radiation damping material contained in slats 106, curtain assembly 100 substantially prevents or limits radiation 34 from exiting housing 16 through inlet 18 and outlet 20, as described above. Conveyor 12 transports object 24 from CT plane 38 through second curtain assembly 101 in a similar, but reversed, sequence as curtain assembly 100.

Figure 7:
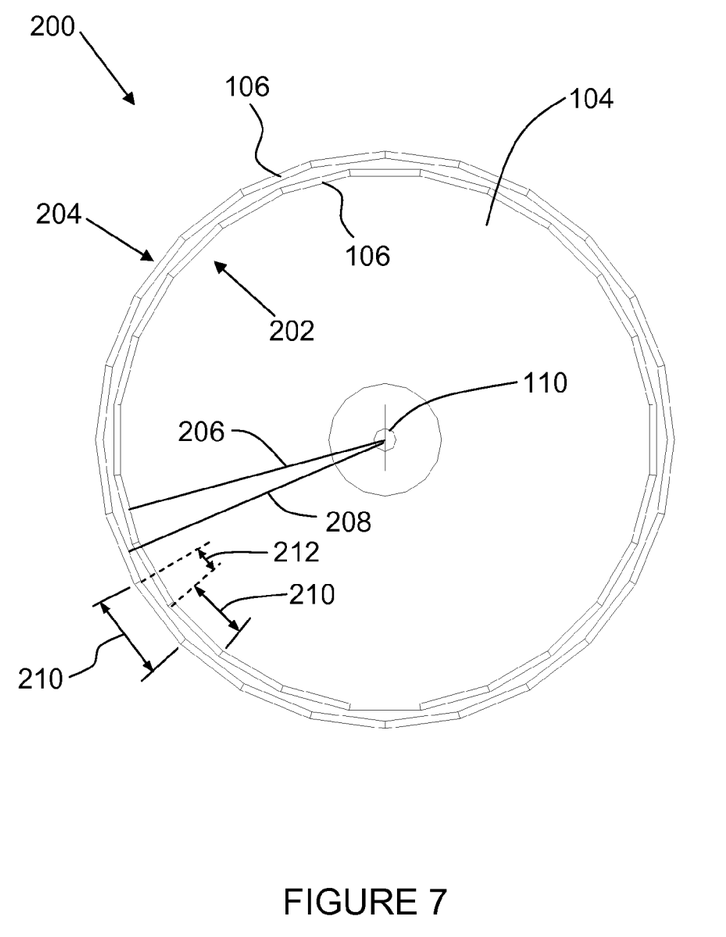
FIG. 7 is a top view of an alternative curtain that may be used with the curtain assembly shown in FIG. 3.

FIG. 7 is a top view of an alternative curtain 200 that may be used with curtain assembly 100 (shown in FIG. 3). Unless otherwise specified, curtain 200 is substantially similar to curtain 102 (shown in FIG. 3), and similar components shown in FIG. 7 are labeled with the same reference numbers used in FIGS. 3-6. In the alternative embodiment, curtain 200 includes an inner drum 202 and an outer drum 204. Inner drum 202 and outer drum 204 are each substantially circumscribed by a plurality of slats 106 that hang vertically from top portion 104. Alternatively, inner drum 202 and/or outer drum 204 include a single slat 106 that substantially circumscribes inner drum 202 and/or outer drum 204. While FIG. 7 shows curtain 200 including inner drum 202 and outer drum 204, curtain 200 may include any suitable number of drums arranged in any suitable configuration. In the alternative embodiment, inner drum 202 and outer drum 204 are substantially circular or disk-shaped, and are circumferentially spaced about center 110 of top portion 104. Inner drum 202 includes an inner drum radius 206 that extends from center 110 to slats 106 of inner drum 202, and outer drum 204 includes an outer drum radius 208 that extends from center 110 to slats 106 of outer drum 204. Inner drum radius 206 is smaller than outer drum radius 208. Alternatively, inner drum 202 and outer drum 204 may have any suitable shape and may be positioned in any suitable arrangement with respect to center 110.

In the alternative embodiment, a width 210 of each slat 106 of inner drum 202 is circumferentially offset from width 210 of each slat 106 of outer drum 204. More specifically, width 210 of each slat 106 of outer drum 204 is offset a distance 212 from width 210 of a radially inner slat 106 of inner drum 202. As such, slats 106 of inner drum 202 substantially overlap slats 106 of outer drum 204 with respect to a radius extending from center 110, such as inner drum radius 206 and/or outer drum radius 208. In the alternative embodiment, distance 212 is equal to about half of width 210. Alternatively, distance 212 is any portion of width 210 that provides a suitable overlap between slats 106 of inner drum 202 and slats 106 of outer drum 204, and distance 212 may vary for each slat 106. As such, the configuration of curtain 200 facilitates reducing or eliminating gaps between slats 106 of curtain 200. More specifically, if curtain 200 is rotated in a similar manner as described above with reference to curtain 102, a centrifugal force may act upon slats 106 to displace a portion of slats 106 radially outward from center 110. However, despite such radially outward displacement of slats 106, a radiation protection capability of curtain 200 may be substantially maintained because of the overlap of slats 106 of inner drum 202 and outer drum 204.

Figure 8:
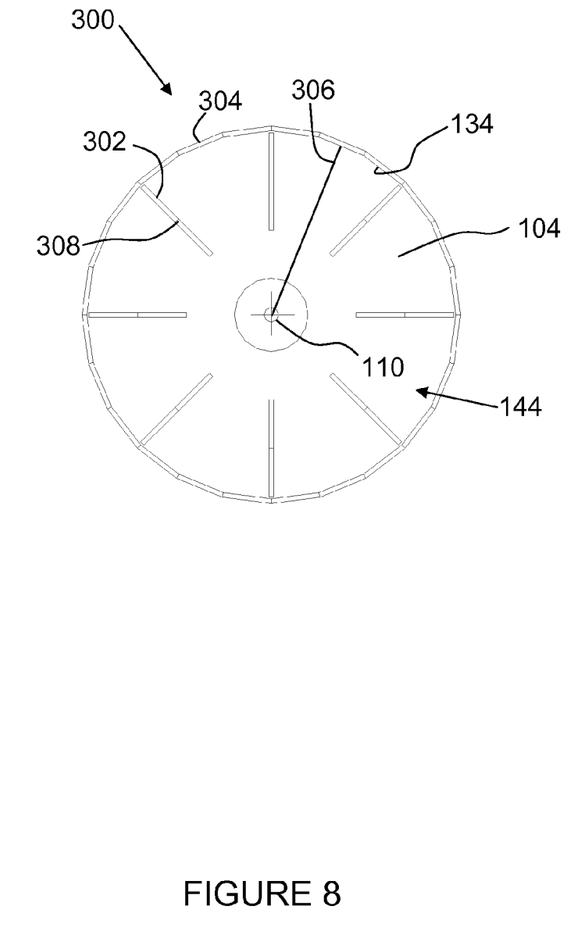
FIG. 8 is a top view of another alternative curtain that may be used with the curtain assembly shown in FIG. 3.

FIG. 8 is a top view of an alternative curtain 300 that may be used with curtain assembly 100 (shown in FIG. 3). Unless otherwise specified, curtain 300 is substantially similar to curtain 102 (shown in FIG. 3), and similar components shown in FIG. 8 are labeled with the same reference numbers used in FIGS. 3-6. In the alternative embodiment, curtain 300 includes a plurality of inner slats 302 and a plurality of outer slats 304. Inner slats 302 and outer slats 304 are substantially similar to slats 106 (shown in FIG. 3). Outer slats 304 are positioned substantially circumferentially about center 110 of top portion 104, and outer slats 304 substantially define outer perimeter 134 and cavity 144. Each outer slat 304 is positioned substantially perpendicularly with respect to a radius 306 extending from center 110 to outer perimeter 134. Alternatively, outer slats 304 are positioned at any suitable angle with respect to radius 306.

In the alternative embodiment, inner slats 302 are positioned substantially parallel to radius 306, and inner slats 302 extend substantially from outer perimeter 134 to center 110 to form a plurality of radial slats 308. Each inner slat 302 and/or radial slat 308 extends at least partially through cavity 144. While FIG. 8 shows each radial slat 308 having two inner slats 302, each radial slat 308 may include any suitable number of inner slats 302, including a single inner slat 302, that extend between outer perimeter 134 and center 110. In one embodiment, each radial slat 308 extends only partially from outer perimeter 134 to center 110. As described herein, the configuration of curtain 300 facilitates maintaining a radiation protection capability of curtain 300. More specifically, if curtain 300 is rotated in a similar manner as described above with reference to curtain 102, a centrifugal force may act upon outer slats 302 to displace a portion of outer slats 302 radially outward from center 110. However, the centrifugal force may not significantly displace inner slats 302 and/or radial slats 308 because the centrifugal force is substantially parallel to the orientation of inner slats 302 and/or radial slats 308 (i.e., substantially parallel to radius 306). As such, a radiation protection capability of curtain 300 may be substantially maintained during rotation of curtain 300.

Figure 9:
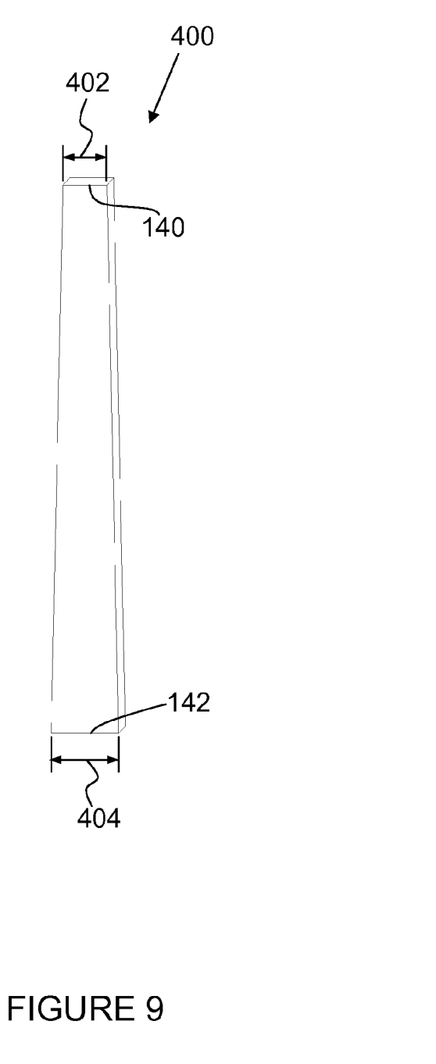
FIG. 9 is a perspective view of an alternative slat that may be used with the curtain assembly shown in FIG. 3.

FIG. 9 is a perspective view of an alternative slat 400 that may be used with curtain assembly 100 and/or with curtain 102 (both shown in FIG. 3), curtain 200 (shown in FIG. 7), and/or curtain 300 (shown in FIG. 8). Unless otherwise specified, slat 400 is substantially similar to slat 106 (shown in FIG. 3), and similar components shown in FIG. 9 are labeled with the same reference numbers used in FIGS. 3-6. In the alternative embodiment, slat 400 includes slat top 140 that has a top width 402, and slat bottom 142 that has a bottom width 404. Top width 402 is smaller than bottom width 404 such that slat 400 tapers from slat bottom 142 to slat top 140. Alternatively, slat 400 may have a flared shape from slat top 140 to slat bottom 142, or any suitable shape. In the alternative embodiment, a plurality of slats 400 are positioned about top portion 104 (shown in FIG. 3) of curtain 102, curtain 200, and/or curtain 300 such that slat top 140 of each slat 400 substantially abuts, or overlaps, slat top 140 of adjacent slats 400. In such a configuration, because bottom width 404 is larger than top width 402, bottom width 404 of each slat 400 overlaps with bottom width 404 of adjacent slats 400. As described herein, the configuration of slat 400 facilitates maintaining a radiation protection capability of curtain 102, curtain 200, and/or curtain 300. More specifically, if curtain 102, curtain 200, and/or curtain 300 are rotated in a similar manner as described above with reference to curtain 102, a centrifugal force may act upon slats 400 to displace a portion of slats 400 radially outward from center 110 (shown in FIG. 3). As slat tops 140 are coupled to top portion 104 (shown in FIG. 3) as described above with reference to FIG. 3, slat bottoms 142 are displaced radially outward from center 110. However, because of the tapered configuration of slat 400, slat bottoms 142 may be substantially maintained in an overlapping or abutting position with respect to adjacent slat bottoms 142. As such, a radiation protection capability of curtain 102, curtain 200, and/or curtain 300 may be substantially maintained during rotation of curtain 102, curtain 200, and/or curtain 300.

The above-described embodiments facilitate protecting an external environment from radiation emitted within a CT scanning system. The curtain assemblies described herein substantially block radiation from exiting through an inlet and/or an outlet of a CT scanning system. Moreover, the curtains within the curtain assemblies rotate in complementary directions to facilitate drawing objects into the CT scanning system and to facilitate reducing a tendency of objects to be repositioned at and/or within an inlet and/or an outlet of the CT scanning system. The curtain assemblies include flexible slats that enable objects to pass through the curtains. The curtain assemblies also include a front group of curtains and a rear group of curtains that further facilitate protecting the external environment from radiation emitted within the CT scanning system. An object may displace one or more slats of a curtain within the front group of curtains, but the rear group of curtains may remain substantially undisturbed until the object has substantially moved past the front group of curtains. As such, an ability to protect the external environment from CT scanning system radiation may remain substantially intact, even when objects are being moved through the curtain assemblies.

A technical effect of the systems and method described herein includes at least one of: (a) allowing objects to pass through curtains with reduced friction, (b) allowing objects to pass through curtains while reducing or preventing changes in object orientation, (c) minimizing and/or counteracting effects of centrifugal force to reduce or prevent radiation leakage, and (d) reducing a misidentification of object boundaries.

Exemplary embodiments of systems and methods for performing a scan of an object are described above in detail. The systems and method are not limited to the specific embodiments described herein, but rather, components of the systems and/or steps of the methods may be utilized independently and separately from other components and/or steps described herein. For example, the methods may also be used in combination with other scanning systems and methods, and are not limited to practice with the computed tomography systems as described herein. Rather, the exemplary embodiment may be implemented and utilized in connection with many other imaging applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A curtain assembly for use with a conveyor having a surface for transporting an object, said curtain assembly comprising:
at least one curtain comprising at least one slat, said at least one curtain is configured to be rotatably coupled to a housing of a scanning system having a radiation source and a detector, said at least one curtain is further configured to facilitate drawing the object into the scanning system housing while substantially preventing radiation emitted from the radiation source from exiting the housing through said at least one curtain, wherein said at least one curtain is configured to rotate about an axis that is not substantially parallel to the surface of the conveyor.

2. A curtain assembly in accordance with claim 1, wherein said at least one curtain further comprises a substantially circular top portion, said at least one slat hangs vertically from said substantially circular top portion.

3. A curtain assembly in accordance with claim 2, wherein said substantially circular top portion has a radius, and said at least one curtain comprises at least one slat positioned substantially perpendicular to the radius of said substantially circular top portion and at least one slat positioned substantially parallel to the radius of said substantially circular top portion.

4. A curtain assembly in accordance with claim 1, wherein said at least one slat tapers from a slat bottom to a slat top.

5. A curtain assembly in accordance with claim 1, wherein said at least one slat at least partially defines a cavity within said at least one curtain.

6. A curtain assembly in accordance with claim 1, wherein said at least one curtain further comprises an inner drum comprising at least one slat and an outer drum comprising at least one slat.

7. A curtain assembly in accordance with claim 1, wherein said at least one curtain further comprises at least two curtains coupled to the housing and a motor configured to rotate said at least two curtains.

8. A curtain assembly in accordance with claim 7, wherein said motor is further configured to rotate a first curtain of said at least two curtains in a first direction and rotate a second curtain of said at least two curtains in a second direction opposite the first direction.

9. A scanning system, comprising:
a housing defining an examination space;
a conveyor comprising a surface, said conveyor configured to transport a stream of objects positioned on said surface through said examination space;
at least one curtain comprising at least one slat, said at least one curtain is rotatably coupled to said housing, wherein said at least one curtain is configured to rotate about an axis that is not substantially parallel to said surface of said conveyor;
a radiation source configured to emit radiation through said examination space; and
a detector configured to detect radiation emitted from said radiation source.

10. A scanning system in accordance with claim 9, wherein said at least one curtain further comprises a substantially circular top portion, said at least one slat hangs vertically from said substantially circular top portion.

11. A scanning system in accordance with claim 10, wherein said substantially circular top portion has a radius and said at least one curtain comprises at least one slat positioned substantially perpendicular to the radius of said substantially circular top portion and at least one slat positioned substantially parallel to the radius of said substantially circular top portion.

12. A scanning system in accordance with claim 9, wherein said at least one slat tapers from a slat bottom to a slat top.

13. A scanning system in accordance with claim 9, wherein said at least one slat at least partially defines a cavity within said at least one curtain.

14. A scanning system in accordance with claim 9, wherein said at least one curtain further comprises an inner drum comprising at least one slat and an outer drum comprising at least one slat.

15. A scanning system in accordance with claim 9, wherein said at least one curtain further comprises at least two curtains coupled to said housing and a motor configured to rotate said at least two curtains.

16. A scanning system in accordance with claim 15, wherein said motor is further configured to rotate a first curtain of said at least two curtains in a first direction and rotate a second curtain of said at least two curtains in a second direction opposite the first direction.

17. A method of assembling a scanning system, the scanning system including a housing, a radiation source configured to emit radiation within the scanning system, and a conveyor having a surface for transporting an object through the housing, said method comprising:
coupling at least one slat to at least one top portion to form at least one curtain; and
rotatably coupling the at least one curtain to the housing, the at least one curtain is configured to facilitate drawing the object into the housing and to substantially prevent radiation from the radiation source from exiting the scanning system through the at least one curtain, wherein the at least one curtain is configured to rotate about an axis that is not substantially parallel to the surface of the conveyor.

18. A method in accordance with claim 17, further comprising rotatably coupling at least two curtains to the housing and coupling the at least two curtains together with a drive chain.

19. A method in accordance with claim 18, further comprising coupling a motor to the drive chain, the motor configured to rotate a first curtain of the at least two curtains in a first direction and rotate a second curtain of the at least two curtains in a second direction opposite the first direction.

20. A method in accordance with claim 17, further comprising coupling an inner drum and an outer drum to the at least one curtain, and coupling at least one slat to each of the inner drum and the outer drum.

* * * * *